(12) United States Patent
Chang et al.

(10) Patent No.: US 11,745,013 B2
(45) Date of Patent: Sep. 5, 2023

(54) METHOD AND SYSTEM FOR TREATING MOVEMENT DISORDERS

(71) Applicants: BIOPRO SCIENTIFIC CO., LTD., Hsinchu (TW); NATIONAL TSING HUA UNIVERSITY, Hsinchu (TW)

(72) Inventors: Pin Chang, Hsinchu (TW); Hsin Chen, Hsinchu (TW); Yen-Chung Chang, Hsinchu (TW); Shih-Rung Yeh, Hsinchu (TW)

(73) Assignees: BIOPRO SCIENTIFIC CO., LTD., Hsinchu (TW); NATIONAL TSING HUA UNIVERSITY, Hsinchu (TW)

( * ) Notice: Subject to any disclaimer, the term of this patent is extended or adjusted under 35 U.S.C. 154(b) by 374 days.

(21) Appl. No.: 16/877,493

(22) Filed: May 19, 2020

(65) Prior Publication Data
US 2020/0368530 A1     Nov. 26, 2020

Related U.S. Application Data

(60) Provisional application No. 62/850,317, filed on May 20, 2019.

(51) Int. Cl.
*A61N 1/36*      (2006.01)
*A61N 2/00*      (2006.01)
*A61N 7/00*      (2006.01)

(52) U.S. Cl.
CPC ..... *A61N 1/36067* (2013.01); *A61N 1/36139* (2013.01); *A61N 2/006* (2013.01); *A61N 7/00* (2013.01); *A61N 2007/0026* (2013.01)

(58) Field of Classification Search
CPC ............ A61N 1/36067; A61N 1/36139; A61N 2/006; A61N 7/00; A61N 2007/0026; A61N 1/0534; A61N 1/205; A61B 5/374
See application file for complete search history.

(56) References Cited

U.S. PATENT DOCUMENTS

| | | | | |
|---|---|---|---|---|
| 5,738,625 A | * | 4/1998 | Gluck | ............... A61N 2/006 128/897 |
| 6,066,163 A | | 5/2000 | John | |
| 6,484,059 B2 | | 11/2002 | Gielen | |

(Continued)

FOREIGN PATENT DOCUMENTS

EP     2004036     12/2008

OTHER PUBLICATIONS

Extended European Search Report of the EP family application EP20175362.1 dated Nov. 12, 2020.

(Continued)

*Primary Examiner* — Mark W. Bockelman
(74) *Attorney, Agent, or Firm* — WPAT, P.C., INTELLECTUAL PROPERTY ATTORNEYS; Anthony King

(57) ABSTRACT

A method for treating movement disorders is provided. The method includes the following operations. A central nervous signal of a patient with movement disorders is recorded. A first stimulation is delivered from a stimulator to the patient when an oscillation episode in a range of from about 3 Hz to about 20 Hz is observed in the central nervous signal. The first stimulation is adapted according to a measurable feature of the oscillation episode. The system for treating movement disorders is also provided.

20 Claims, 10 Drawing Sheets

(56) References Cited

U.S. PATENT DOCUMENTS

| | | | |
|---|---|---|---|
| 7,236,830 | B2 | 6/2007 | Gliner |
| 7,269,456 | B2 | 9/2007 | Collura |
| 7,616,998 | B2 | 11/2009 | Nuttin et al. |
| 7,979,129 | B2 | 7/2011 | Gill |
| 8,676,327 | B2 | 3/2014 | Doerr et al. |
| 8,903,499 | B2 | 12/2014 | Pless et al. |
| 8,923,977 | B2 | 12/2014 | Decré et al. |
| 8,948,875 | B2 | 2/2015 | Paulus et al. |
| 9,014,820 | B2 | 4/2015 | Lee et al. |
| 9,949,376 | B2 | 4/2018 | Greenberg et al. |
| 2003/0149457 | A1* | 8/2003 | Tcheng .............. A61N 1/36135 607/48 |
| 2006/0173510 | A1* | 8/2006 | Besio .................... A61B 5/375 607/45 |
| 2008/0046053 | A1* | 2/2008 | Wagner ................... A61N 2/02 607/116 |
| 2015/0202447 | A1* | 7/2015 | Afshar ............... A61N 1/36171 600/378 |
| 2018/0110991 | A1 | 4/2018 | Molnar et al. |

OTHER PUBLICATIONS

Dejean C, Gross CE, Bioulac B, Boraud T. Dynamic changes in the cortex-basal ganglia network after dopamine depletion in the rat. J Neurophysiol. Jul. 2008;100(1):385-396.

Dejean C, Gross CE, Bioulac B, Boraud T. Synchronous high-voltage spindles in the cortex-basal ganglia network of awake and unrestrained rats. Eur J Neurosci. Feb. 2007;25(3):772-784.

Rémi Souriau, Vincent Vigneron, Jean Lerbet, Hsin Chen. Boltzmann Machines for signals decomposition. Application to Parkinson's Disease control. GRETSI, Aug. 2019, Lille, France.

Rémi Souriau, Dominique Fourer, H. Chen, Jean Lerbet, Hichem Maaref, et al. High-Voltage Spindles detection from EEG signals using recursive synchrosqueezing transform. GRETSI, Aug. 2019, Lille, France.

R. Perumal, V. Vigneron, C. Chuang, Y. Chang, S. Yeh, H. Chen. An efficient algorithm for predicting pathological high-voltage spindles related to Parkinsonian resting tremor from local field potential recordings [abstract]. Mov Disord. Oct. 7, 2018; 33 (suppl 2).

Rémi Souriau, Vincent Vigneron, Jean Lerbet, Hsin-Chen Chen. Probit latent variables estimation for a gaussian process classifier: Application to the detection of high-voltage spindles. 14th International Conference on Latent Variable Analysis and Signal Separation (LVA/ICA Jul. 2018, Guildford, United Kingdom, pp. 514-523.

Y.-C. Chen, R. Perumal, C.-H. Hwang and H. Chen. Hardware-based simplified discrete wavelet transform for detecting high-voltage spindles in neuron signals. 2017 IEEE International Instrumentation and Measurement Technology Conference (I2MTC), Turin, Italy, May 22-25, 2017, pp. 1-5.

Yu-Chieh Chen, Ching-Chih Chang, Ramesh Perumal, Shih-Rung Yeh, Yen-Chung Chang, and Hsin Chen. 2019. Optimization and Implementation ofWavelet-based Algorithms for Detecting High-voltage Spindles in Neuron Signals. ACM Trans. Embed. Comput. Syst. 18, 5, Article 39 (Jul. 2019), 16 pages.

* cited by examiner ns application claims the benefit of prior-filed U.S.
METHOD AND SYSTEM FOR TREATING MOVEMENT DISORDERS

CROSS REFERENCE TO RELATED APPLICATION

This application claims the benefit of prior-filed U.S. provisional application No. 62/850,317, filed on May 20, 2019, and incorporates its entirety herein.

FIELD

The present disclosure relates to a method and system for treating movement disorders, particularly, to a method and system that delivers stimulations to the brain once an abnormal electrical activity related to movement disorders is observed.

BACKGROUND

Abnormal electrical activity may be observed as an oscillation of brainwave. The oscillations may be classified by frequency, for example, some of the oscillations may have a range of from about 3 Hz to about 20 Hz, which may be called as mu wave when such oscillation is observed in human beings. Similar oscillations may be observed in other animals. For example, High-Voltage Spindle (HVS) is the wave analogous to mu wave which may be observed in rodent.

BRIEF DESCRIPTION OF THE DRAWINGS

Aspects of the present disclosure are best understood from the following detailed description when read with the accompanying figures. It is noted that, in accordance with the standard practice in the industry, various structures are not drawn to scale. In fact, the dimensions of the various structures may be arbitrarily increased or reduced for clarity of discussion.

DETAILED DESCRIPTION

Figure 1:
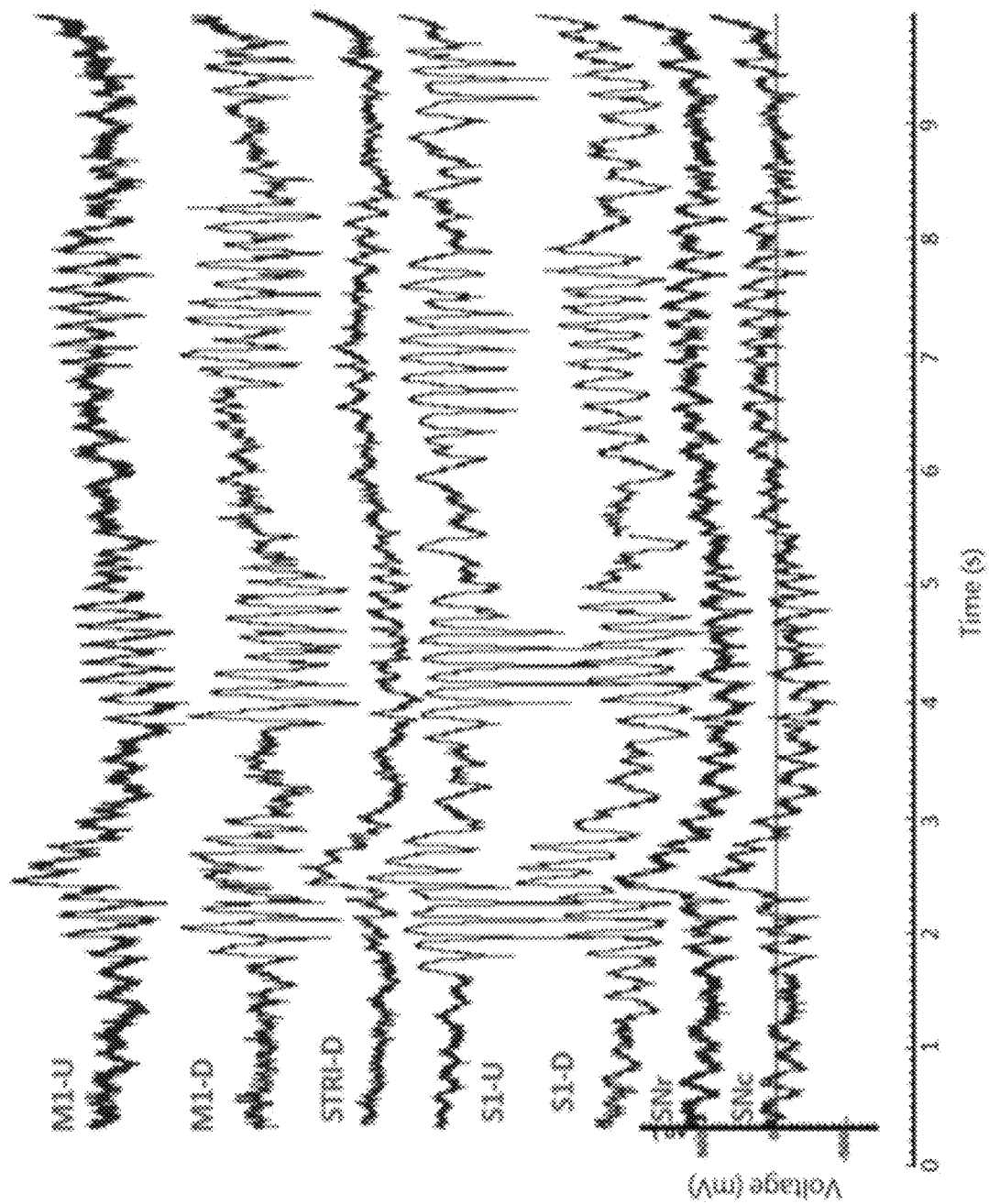
FIG. 1 illustrates the oscillation episode in the range of from about 5 Hz to about 13 Hz may be detected almost simultaneously in different areas of a brain.

The following disclosure provides many different embodiments, or examples, for implementing different features of the provided subject matter. Specific examples of elements and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper", "on" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

As used herein, the terms such as "first", "second" and "third" describe various elements, components, regions, layers and/or sections, these elements, components, regions, layers and/or sections should not be limited by these terms. These terms may be only used to distinguish one element, component, region, layer or section from another. The terms such as "first", "second", and "third" when used herein do not imply a sequence or order unless clearly indicated by the context.

Mu wave and its corresponding waves (e.g., HVS) are brainwave pattern appearing only when the subjects are in an awake, immobile state (or idling state). On a rodent modeling the Parkinson's disease, HVS wave represents the synchronization of oscillatory activities in cortical-basal ganglia networks. HVS wave appears more frequently and in longer episodes than those on rodents without Parkinson's disease. Mu wave and HVS (collectively "brainwave pattern associated with movement disorder") can be observed through electroencephalography (EEG) or local field potentials (LFP) recordings. The duration of each HVS oscillation episode (the period of the continuous appearance of brainwave pattern associated with movement disorder) may continue for 1 to 4 seconds, and the onset and termination of each oscillation episode could occasionally vary across the cortical-basal ganglia structures. Refer to FIG. 1, according to the brainwave observation on rats, the LFP recordings show HVS (the oscillations occur from about 1.5 second to about 3 second, from about 3.8 second to about 5.4 second, and from about 6.3 second to about 8.2 second) may be observed almost simultaneously in different areas of basal ganglia, includes dorsal striatum (STRI-D), substantia nigra pars compacta (SNc), substantia nigra pars reticulata (SNr), and different areas of cerebral cortex such as the primary motor cortex (M1-upper layers, M1-deeper layers) and the somatosensory cortex (S1-upper layers, S1-deeper layers).

The more frequent appearance of HVSs has been considered as an early indicator of Parkinson's disease (PD). PD is a severely disabling neurodegenerative movement disorder with insidious pathogenesis in the cortical-basal ganglia networks, where the HVS happens originally. In recent decades, deep brain stimulation (DBS) has been researched and practiced worldwide for treating PD. This surgical procedure involves implanting electrodes within several deep areas of brain, such as subthalamic nucleus (STN) or globus pallidus (GPi). These implanted electrodes produce electrical impulses that regulate abnormal impulses in the patient's brain, and thus releasing PD symptoms. Nevertheless, this treatment of PD still needs improvements for reducing adverse side-effects and enhancing efficacy.

The present disclosure provides a method for treating movement disorders includes PD and some Parkinsonian syndromes such as bradykinesia, dystonia, rigidity, gait disorders, and essential tremor. This method is a closed-loop stimulation method by the mechanism of neuromodulation which applies stimulation once the central nervous signal from spinal cord or brain (e.g., brainwave pattern) associated with movement disorder is observed. In other words, the present disclosure is a treatment which the detection or observation of central nervous signal pattern associated with movement disorder is used as a feedback to trigger or control the stimulation. In some embodiments, the closed-loop stimulation method disclosed by the present disclosure may be further applied to several neurological disorders or brain dysfunctions such as Alzheimer's disease (AD), epilepsy, stroke, traumatic brain injury (TBI), pain, coma, paralysis, Tourette syndrome, tinnitus, depression, obsessive-compulsive disorder (OCD), or headache. In other words, the present disclosure may be utilized to different neurological disorders or brain dysfunctions, depends on the different brainwave patterns being detected or observed.

Figure 2A:
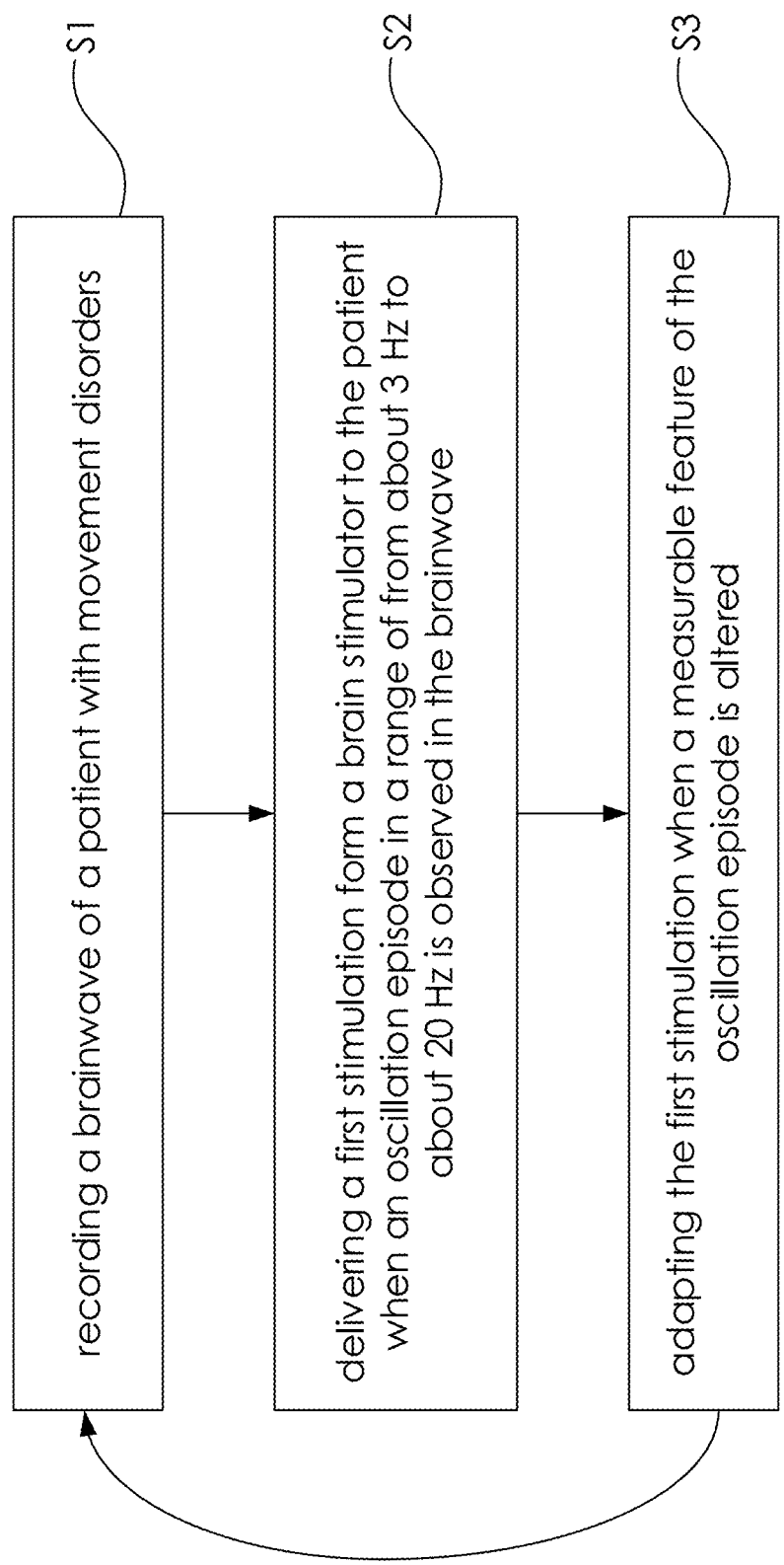
FIG. 2A illustrates the operations of the closed-loop treatment according to some embodiments of the present disclosure.

As shown in FIG. 2A, in some embodiments, the treatment includes following operations: recording a central nervous signal of a patient with movement disorders (step S1); delivering a first stimulation from a stimulator to the patient when an oscillation episode in a range of from about 3 Hz to about 20 Hz is observed in the central nervous signal (step S2); adapting the first stimulation according to a measurable feature of the oscillation episode (step S3).

Figure 3A:
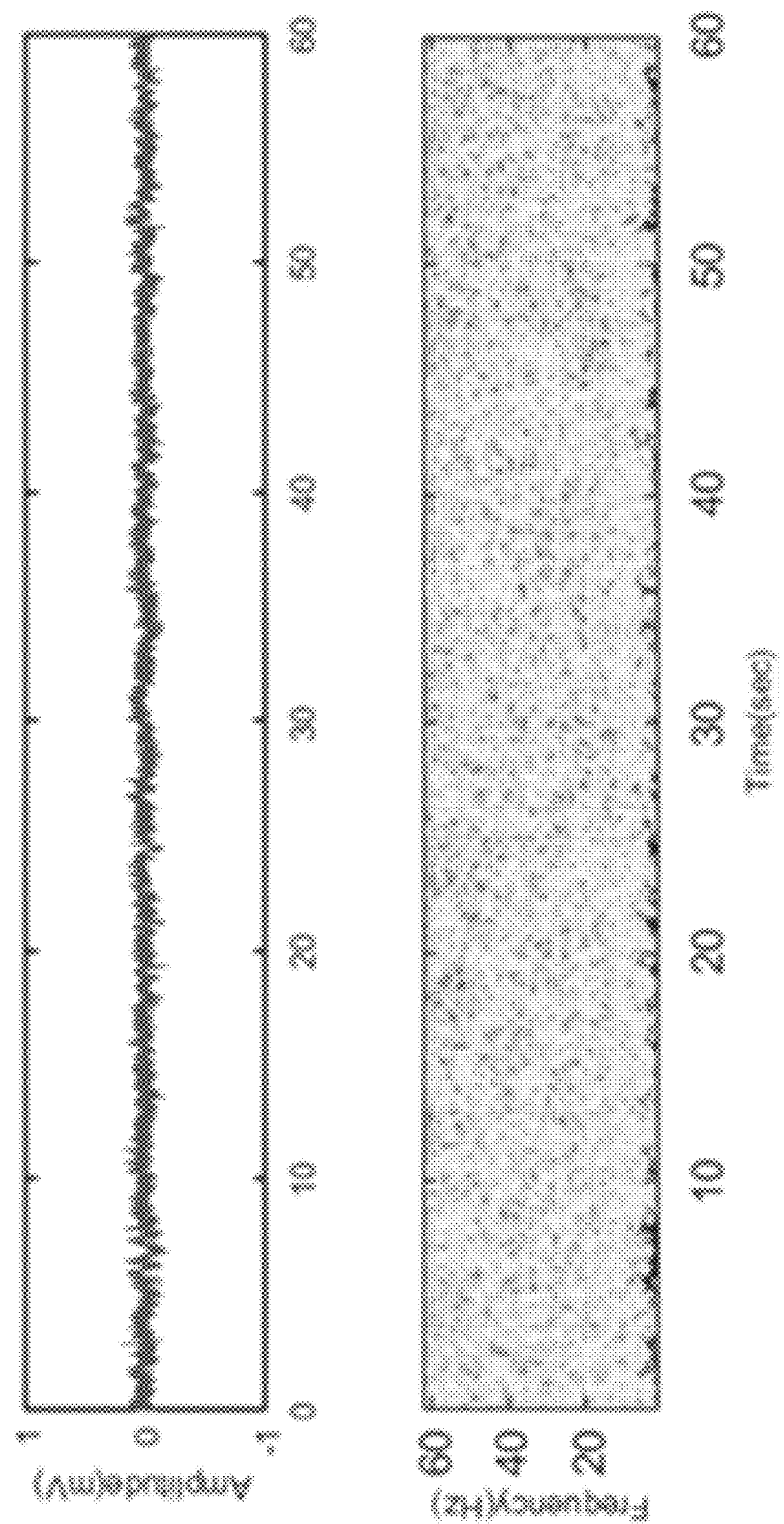
FIG. 3A illustrates a brainwave of rat prior to Parkinson's disease is induced in some embodiments of the present disclosure.
Figure 3B:
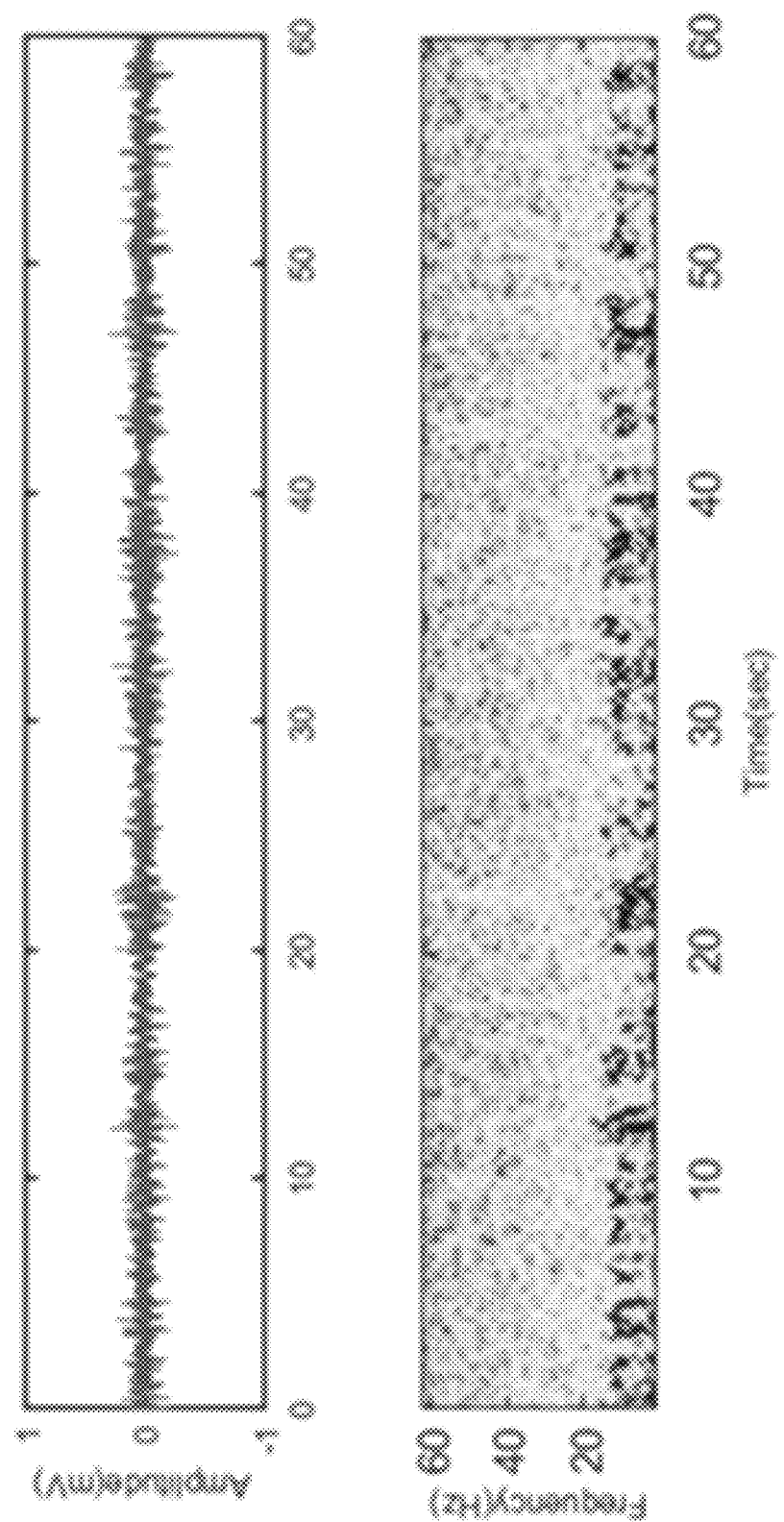
FIG. 3B illustrates a brainwave of rat after Parkinson's disease is induced in some embodiments of the present disclosure.

The oscillation episode in the frequency range of from about 3 Hz to about 20 Hz may be utilized as an observing target in determining whether to deliver the first stimulation based on the relationship between the oscillation episode and the neural disorders such as Parkinson's disease. As shown in FIG. 3A, according to the brainwave recording on a rat, there is no notably oscillation episode in the frequency range of from about 3 Hz to about 20 Hz prior to inducing Parkinson's disease in the rat can be observed. As shown in FIG. 3B, after Parkinson's disease is induced in the rat by injecting substances such as Haloperidol, the oscillation episodes in the frequency range of from about 3 Hz to about 20 Hz may be observed clearly. Therefore in some embodiments of the present disclosure, the abovementioned frequency range may be utilized as a pathological signature to trigger the stimulation automatically.

In some embodiments, the stimulator may be an implanted electrical signal generator. In some other embodiments, the stimulator may be a non-invasive system which includes transcranial magnetic stimulation, transcranial direct-current stimulation, and focused ultrasound.

In some embodiments, the measurable feature of the oscillation episode may be recorded before or during delivering the first stimulation, and the measurable feature obtained may thus be used for adapting the first stimulation. In some embodiments, the measurable feature includes an oscillation intensity and an oscillation frequency. In some embodiments, the measurable feature may further include an oscillation duration of the oscillation episode and a frequency of occurrence of the oscillation episode within a predetermined timeframe.

To be more detailed, the adaptation of the first stimulation may be achieved through different approaches, in other words, more than one stimulation form may be determined according to the measurable feature. In some embodiments, the stimulation form includes at least one of a stimulation frequency, a stimulation intensity, and a stimulation waveform, and any of them may be changed according to the measurable feature of the oscillation episode. In some embodiments, the stimulation intensity may include an amplitude of the stimulation. In some embodiments, the stimulation form may further include a stimulation duration and a frequency of occurrence of the stimulation.

In some embodiments, the measurable feature can be an energy of derived from an oscillation episode. For example, the first stimulation can be adapted from a higher stimulation intensity to a lower stimulation intensity once the energy derived from the oscillation episode is measured to be half of its original value (e.g., at the onset of the oscillation episode). For another example, the stimulation intensity is changed once the oscillation intensity is measured to be one-third of its original value (e.g., at the onset of the oscillation episode).

The measurable features for adapting the stimulation may be acquired by different approaches depending on the nature thereof. For instance, the oscillation intensity and the oscillation frequency may be recorded in real time and to be used for determining a real time feedback, for example, adapting the stimulation in real time. On the other hand, oscillation duration of the oscillation episode and the frequency of occurrence of the oscillation episode may be determined within a predetermined timeframe, for example, a predetermined time window when a plurality of oscillation episodes take place, and to be used for determining an average feedback with respect to the predetermined timeframe. In some embodiments, the average feedback may not lead to real time adaptation of the stimulation but may associate with the determination of the subsequent stimulation form. In some embodiments, the oscillation duration of the oscillation episode is determined by averaging the durations of at least three oscillation episodes, two oscillation episodes, or one oscillation episode. In some embodiments, the frequency of occurrence of the oscillation episode may be calculated within a suitable timeframe, for example, in one hour, thirty minutes, or fifteen minutes.

In using the oscillation duration as a measurable feature for adapting stimulations, the first stimulation may be adapted from a longer stimulation duration to a shorter stimulations duration once the oscillation duration is measured to be shorter than a predetermined reference level, for instance, about 50% shorter than its original averaged value (e.g., the averaged oscillation durations within a specific timeframe). Generally, the oscillation duration may be significantly shortened after the stimulation, for example, from about 3.0 seconds (prior to applying stimulation) to less than about 1.0 second (after applying stimulation). In some embodiments, the stimulation may be applied until the oscillation is no longer observed on the recording, and hence comparatively long stimulation duration was adopted. In some other embodiments, the stimulation can be adapted or paused or terminated when the oscillation is still observable on the recording, and the oscillation may be suppressed instantly after the stimulation is adapted or paused or terminated, thereby comparatively short stimulation duration may be adopted. In some embodiments, the first stimulation duration is applied for longer stimulation duration, and the follow-up stimulations durations may be adapted to be about 70% or even 80% shorter than the first stimulation duration. In some embodiments, the follow-up stimulations can be automated by the closed-loop system described herein with constantly-adapting stimulation duration based on various factors.

In using the frequency of occurrence of the oscillation episode as a measurable feature for adapting stimulations, the intensity of the first stimulation may be adapted to be greater once the frequency of occurrence of the oscillation episode is greater than a predetermined reference level, for instance, about 50% greater than its original averaged value (e.g., the averaged frequency of occurrence of the oscillation episodes within a specific timeframe).

In some embodiments, prior to applying the first stimulation to the patient, a reference level calibration, or a baseline calibration, may be conducted when the measurable feature involves the oscillation duration and/or the frequency of occurrence of the oscillation episode of the central nervous signal.

Although the oscillations may be suppressed by applying the stimulation at once, in some embodiments, the oscillations may not need to be suppressed entirely because the oscillations may be observed in a normal central nervous signal occasionally. In some embodiments, more than one measurable features are used for adapting stimulations, and therefore the adapted first stimulation may be different from the pre-adapted first stimulation both in frequency and duration, for example.

After adapting the first stimulation according to at least one of the measurable features of the oscillation episode, the treatment continues to repeat the step S1 thereby forming a closed-loop procedure.

Figure 2B:
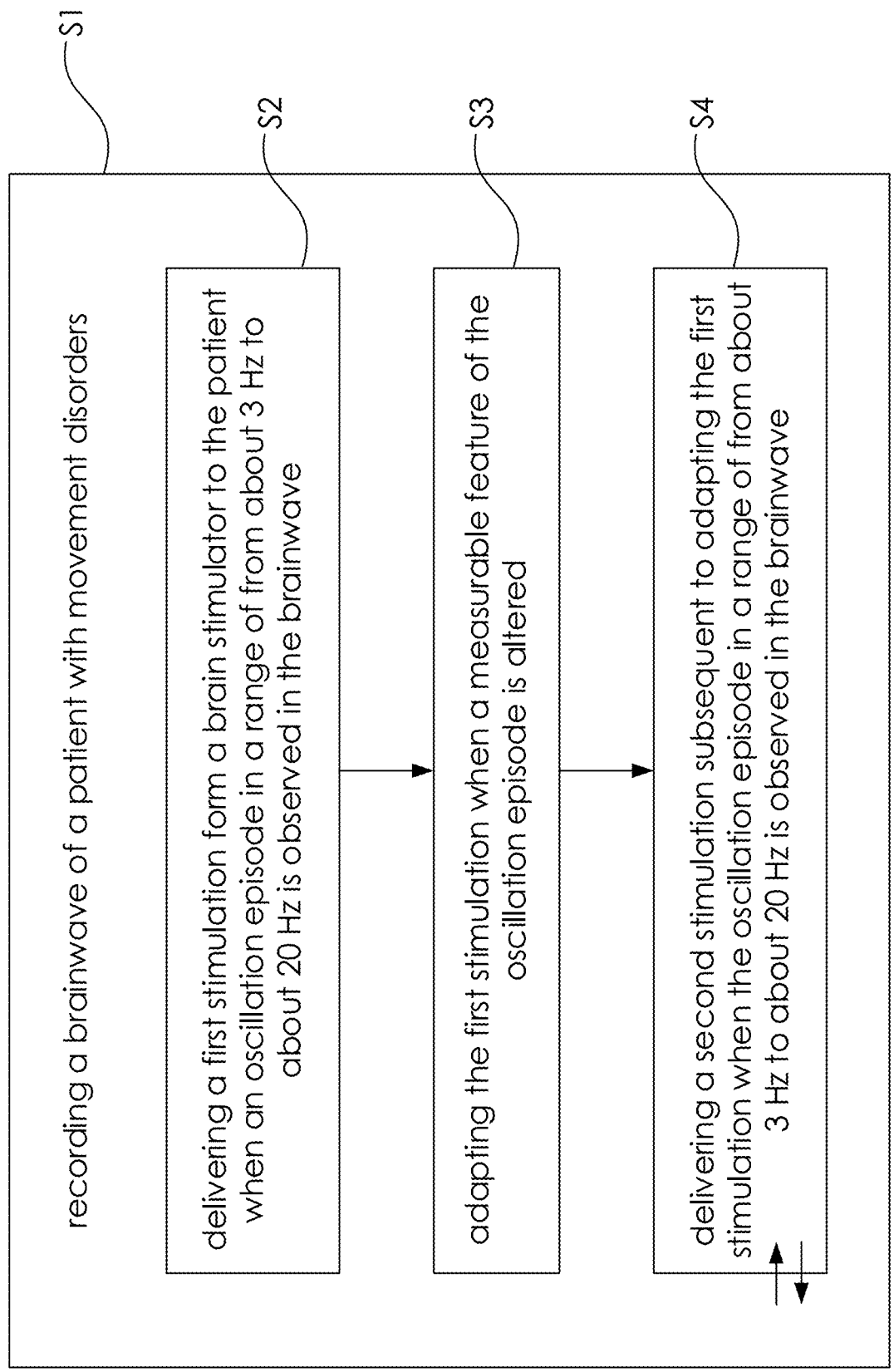
FIG. 2B illustrates the operations of the closed-loop treatment according to some embodiments of the present disclosure.

Moreover, for a treatment with a closed-loop procedure, the recording of the central nervous signal is continued and the system awaits another adequate time to deliver a subsequent, or a second stimulation. The second stimulation subsequently applied may or may not be the same as the first stimulation or the adapted form of the first stimulation. As shown in FIG. 2B, in some embodiments, the treatment includes following operations: recording a central nervous signal of a patient with movement disorders (step S1); delivering a first stimulation from a stimulator to the patient when an oscillation episode in a range of from about 3 Hz to about 20 Hz is observed in the central nervous signal (step S2); adapting the first stimulation according to a measurable feature of the oscillation episode (step S3); and delivering a second stimulation subsequent to adapting the first stimulation when another oscillation episode in a range of from about 3 Hz to about 20 Hz is observed in the central nervous signal (step S4). As previously discussed, the measurable features of the oscillation episode may include the oscillation intensity, the oscillation frequency, the energy derived from the oscillation episode, the oscillation duration of the oscillation episode, and the frequency of occurrence of the oscillation episode. The details of the second stimulation in step S4 will be described later.

In some embodiments, LFP signals are monitored in step S1 by implanting a plurality of microelectrodes in, for example, the extracellular space in brain tissue. The LFP recordings from the microelectrodes are analyzed in step S1 to identify the mu wave, for example, whether there is an oscillation signal in the range of from about 3 Hz to about 20 Hz. In some embodiments, the analysis process is achieved by using time-frequency (TF) analysis to extract the distinctive features of mu wave. In some embodiments, continuous wavelet transform (CWT) is selectable to detect the characteristic of mu wave. In some embodiments, the algorithm to some second-order statistics is also available to identify mu wave so that the present disclosure may combine with field-programmable gate array (FPGA)-based real time systems.

In some embodiments, before recording the central nervous signal from a first region of the brain of the patient with movement disorders, a stimulation lead coupling to an electrical signal generator is implanted to a second region of the brain. The first region and the second region may or may not be the same region of the brain. In some embodiments, the first region and the second region is the same, and therefore only one lead may be used in such region for recording and stimulating, which means a less invasive approach in treating is achieved. In some other embodiments, the first region and the second region are different, and therefore less noises or unwanted signals from the stimulation lead may interfere the signal being recorded. In some embodiments, as aforementioned and shown in FIG. 1, HVS may be observed in different areas of the brain of rats, such as basal ganglia and cortex, and the stimulation may be applied to the subthalamic nucleus (STN) or globus pallidus (GPi) of the brain. In some embodiments, HVS may be observed in basal ganglia and cortex of the brain of rats, and the stimulation may be applied to cerebral cortex such as the primary motor cortex (M1-U, M1-D) and the somatosensory cortex (S1-U, S1-D) of the brain.

Figure 4:
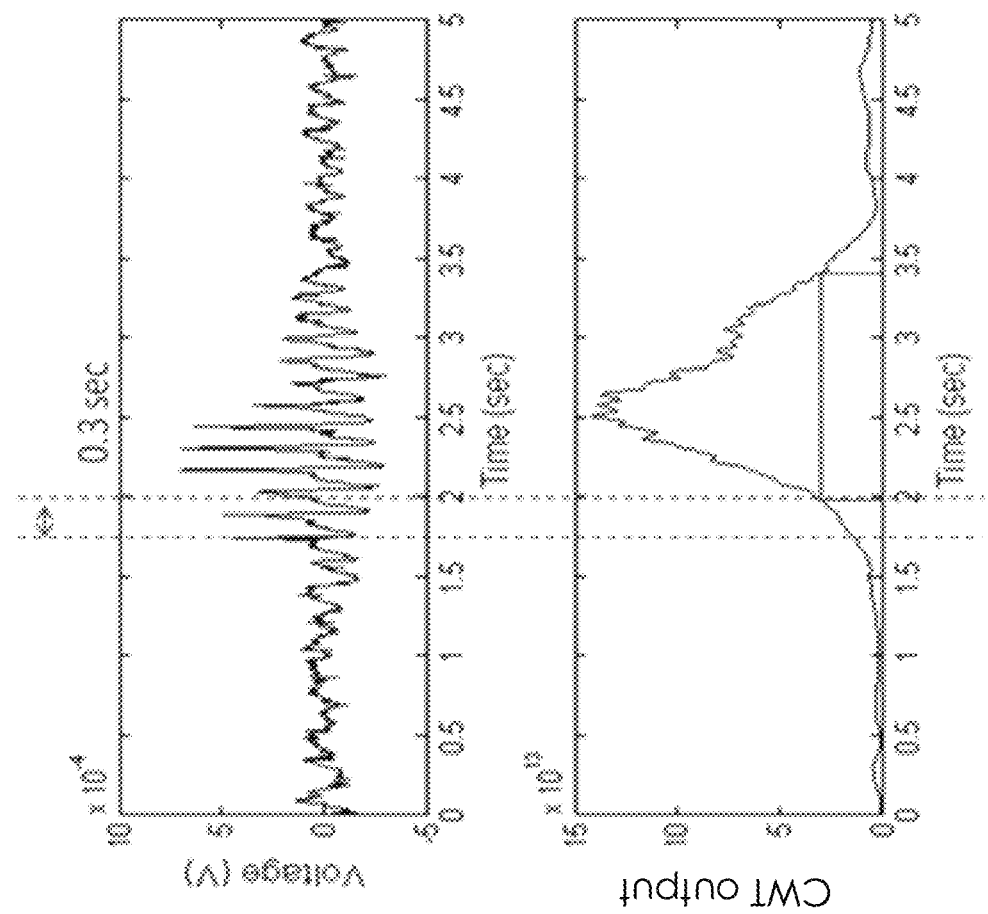
FIG. 4 illustrates a recorded HVS episode and the stimulation delivered in some embodiments of the present disclosure.

As shown in FIG. 4, according to the brainwave observation of rats, the HVS signal identification may be completed in early stage before the energy of HVS substantially breakout. The upper part of FIG. 4 shows the amplitude of brainwave monitored by LFP. The lower part of FIG. 4 shows the TF analysis of the upper part of FIG. 4. In some embodiments, the HVS signal identification shown in upper part of FIG. 4 takes 0.3 seconds, and the stimulation is delivered immediately thereafter as shown in red solid line in the lower part of the figure. The stimulation may be terminated at a point when the HVS is decaying to a lower threshold, terminated, or after the HVS is terminated.

When brainwave pattern associated with movement disorder is identified, the stimulation is delivered from a brain stimulator in step S2. In some embodiments, the stimulation parameters (e.g., including, but not limited to, stimulation intensity) of the treatment are fixed. In some embodiments, the stimulation parameters of the treating loop can be determined by the one or more calibration round carried out prior to the first stimulation of the closed-loop treatment. For example, the voltage and current may be changed among different subject, or patients, when applying stimulation. The proper voltage and current, or the stimulation intensity, may be determined taking into account a desired suppression period. That is, the stimulation intensity may be determined in order to achieve a desired stimulation duration among which the brainwave pattern associated with movement disorder is effectively suppressed. Such stimulation intensity determination may be carried out in the calibration rounds and such parameters can be used in the following closed-loop treatment. Of course in other embodiments, the stimulation intensity determination can take place at during an initial period of the closed-loop treatment.

In some embodiments, according to the brainwave observation of rats, the first stimulation of the closed-loop treatment is terminated when HVS is decayed significantly as shown in the example in the lower part of FIG. 4. In some embodiments, the first stimulation can be terminated after HVS is no longer observed. In order to suppress HVS completely, in some embodiments, the stimulation duration of the first stimulation is longer than a HVS wave episode. In some embodiments, the stimulation duration is longer than the HVS wave episode by 1.0 to 2.0 seconds. In some embodiments, the stimulation duration is shorter than the HVS wave episode.

For instance, when the HVS wave episode continues for 3 seconds, the first stimulation delivered right after the identification of HVS wave to the brain can be sustained from about 4 seconds to about 5 seconds. In some embodiments, the stimulation is terminated or reduced before the HVS wave is entirely suppressed, in other words, the HVS wave may be suppressed to a certain extent if the stimulation is delivered timely.

During step S1, step S2, and step S3, recording of the central nervous signal is continued as a mean for determining the onset and the offset of the oscillation episode associated to movement disorder. In some embodiments, the recording of the central nervous signal may not include data storing, that is, the central nervous signal may be only for detecting in real time without being stored for further analysis. Then in step S4, the second stimulation may be delivered when a subsequent HVS wave is identified in some embodiments, the second stimulation is applied with the stimulation intensity determined according to the calibration round prior to the first stimulation or initial stage of the closed-loop treatment. In some embodiments, the second stimulation in step S4 may be terminated as same as the first stimulation that after the HVS wave is no longer observed, which means the termination of the second stimulation is dependent on the observation of the HVS wave independently. In some embodiments, the second stimulation in step S4 may be delivered and following the stimulation intensity of the first stimulation. An adapted form of the second stimulation may be carried out as those described in FIG. 2A. Similar to the embodiment as shown in FIG. 2A, the recording of the central nervous signal is continued and the system awaits another adequate time to deliver another second stimulation after step S4.

In some embodiments, the first stimulation and the second stimulation are electrical stimulations with a frequency in the range of from about 100 Hz to about 180 Hz. In some embodiments, the frequency is in the range from about 10 Hz to about 10K Hz. In some embodiments, the frequency is depends on the demand of different types of treating purposes or clinical treating progresses and thus not limited to the ranges as aforementioned. In some embodiments, the first stimulation and the second stimulation may be provided by infrared neural stimulation (INS). INS may stimulate a brain of a patient by pulsed mid-infrared light which may generate highly controlled temperature transients in neurons.

Figure 5A:
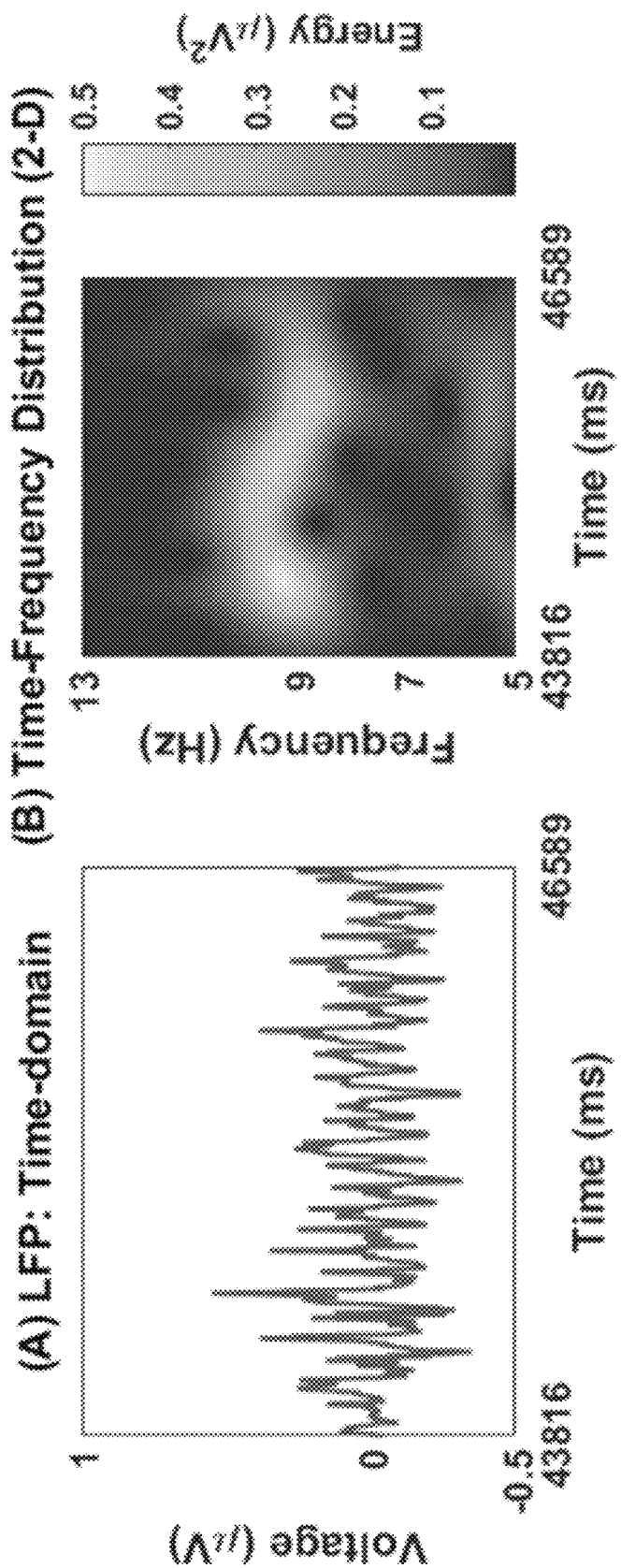
FIG. 5A illustrates the HVS signal and energy of the HVS observed in a PD rat without stimulation, according to a comparative embodiment of the present disclosure.
Figure 5B:
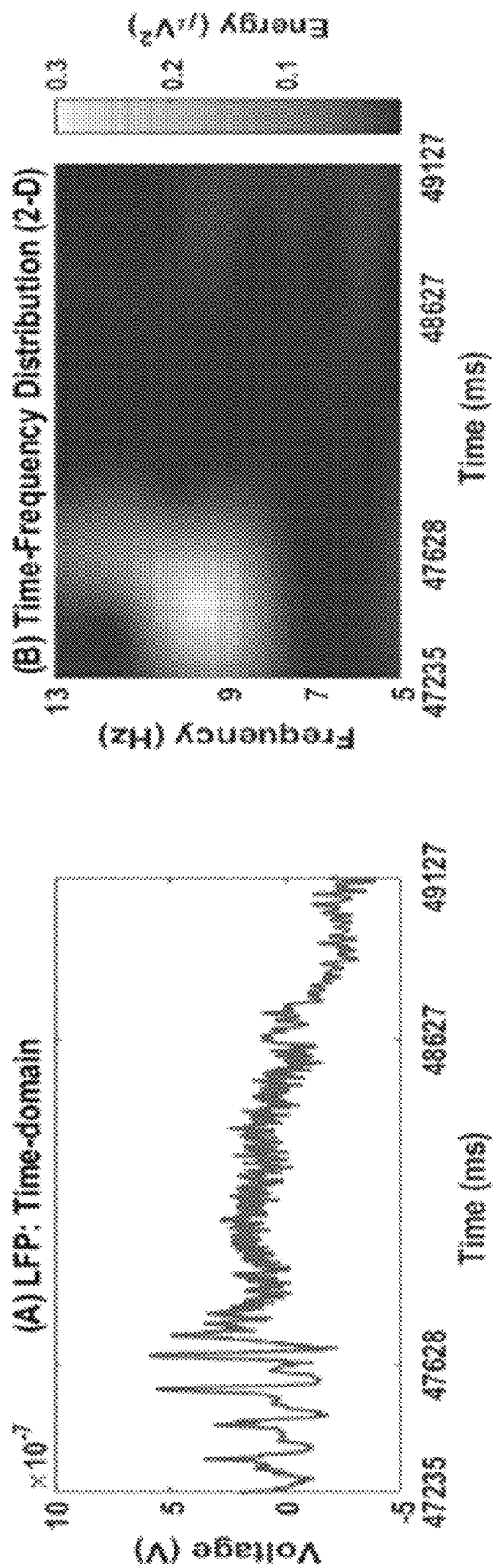
FIG. 5B illustrates the HVS signal and energy of the HVS observed in a PD rat with stimulation, according to an embodiment of the present disclosure.

As shown in FIG. 5A, according to the brainwave observation of rats, without applying stimulation, during the time span of from 43816 ms to 46589 ms, the energy of an HVS episode (in the frequency range of 5 Hz to 13 Hz), is observed constantly during the aforesaid time span. In contrast, as shown in FIG. 5B, when applying stimulation at about 47,628 ms, during the time span of from 47,235 ms to 49,127 ms, the energy of an HVS episode (in the frequency range of 5 Hz to 13 Hz), is first observed between t1 and t2 and subsequently disappeared after the application of the stimulation. As a result of the stimulation, the energy of the HVS episode in rats with PD is suppressed and thus the HVS per se is suppressed. It is well-proved that HVS may be significantly and substantially suppressed or inhibited by stimulation.

Figure 6:
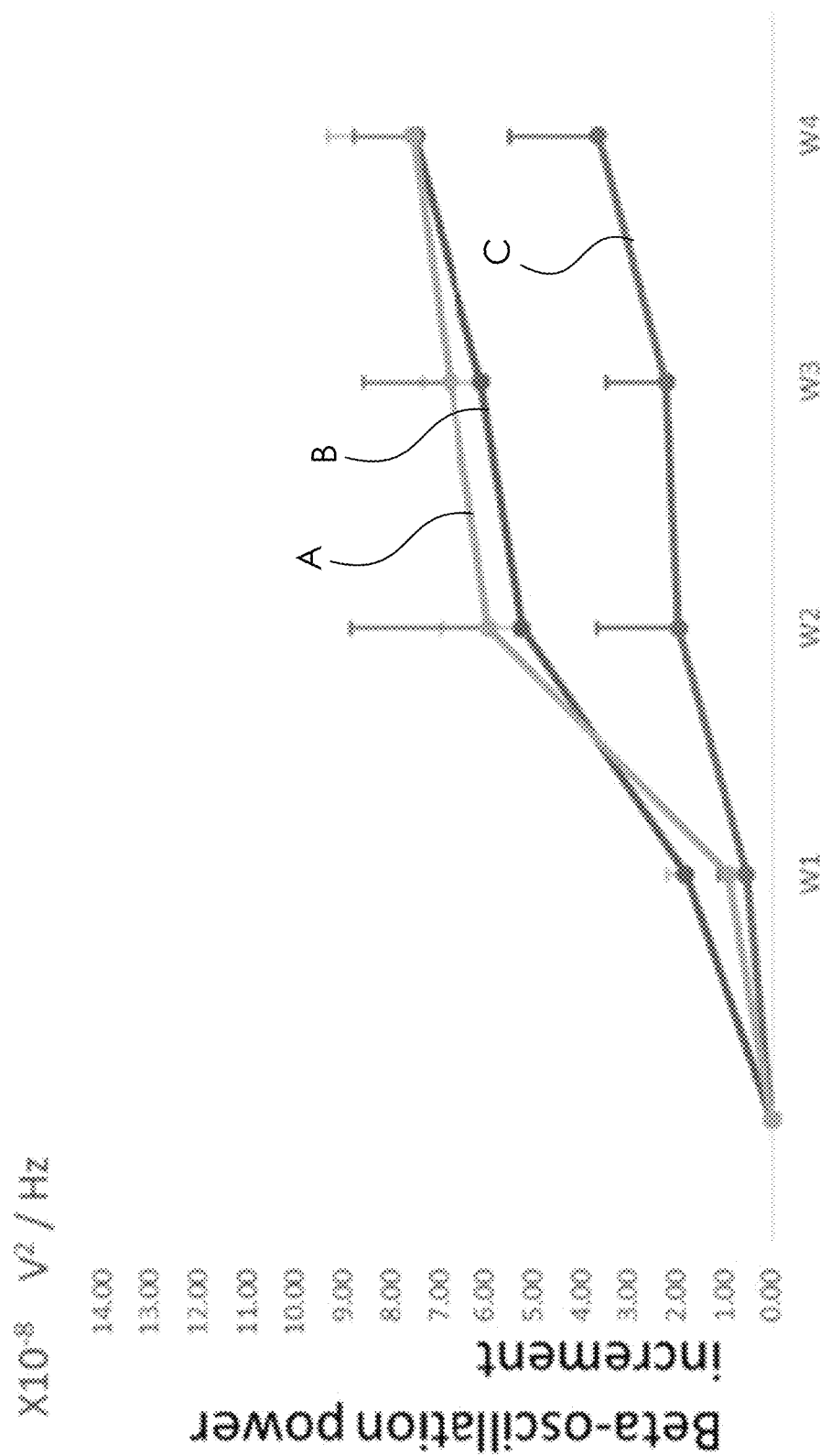
FIG. 6 illustrates the increment rate of beta oscillation may be substantially suppressed by a closed-loop stimulation, according to an embodiment of the present disclosure.

According to the present disclosure, the oscillation episode in the range of from about 3 Hz to about 20 Hz such as the HVS of rats or the mu wave of human beings can be suppressed, silenced or inhibited by using a closed-loop treatment that identifies such oscillation episode as a feedback to automatically trigger or control the stimulation. Moreover, as shown in FIG. 6, in some other embodiments of the present disclosure, the closed-loop treatment may be utilized on suppressing other oscillation having a frequency out of the range as aforementioned. For instance, Beta oscillation is a pathological signature with a frequency from about 20 Hz to about 40 Hz not only being greatly enhanced in PD but also the beta activity at rest and beta changes in response to treatment with Parkinsonian syndromes. By stimulating a portion of the rats with PD 90 minutes daily for 10 days, as shown in FIG. 6, the increment rate of beta oscillation of the rat with PD without any stimulation (scale A) is statistically almost as same as the rats with PD with a random stimulation (scale Random stimulation herein refers to the rat with PD being stimulated randomly, regardless of the identification of HVS. In contrast, by using the closed-loop treatment by regularly applying stimulation after identification of HVS (scale C), the increment rate of beta oscillation is significantly and substantially reduced compared to the red and green scales. As a result, the aforesaid closed-loop treatment can reduce the increment rate of beta oscillation, indicating that the disease progression of PD can be alleviated by such closed-loop treatment.

In some embodiments, the closed-loop treatment can be carried out continuously in delaying the disease progression of PD. In some embodiments, the duration of closed-loop treatment may be carried out less than 2 hours per day to observe sufficient effect. The latter provides an energy-efficient alternative and suitable to lower the frequent of battery replacement surgeries to the patient. In consideration of the nature of stimulation is an intense power which affects the cells and tissues near the stimulation portion strongly, the controlling of stimulation period per day may reduce the side-effect of brain stimulation from excessive stimulation.

Figure 7:
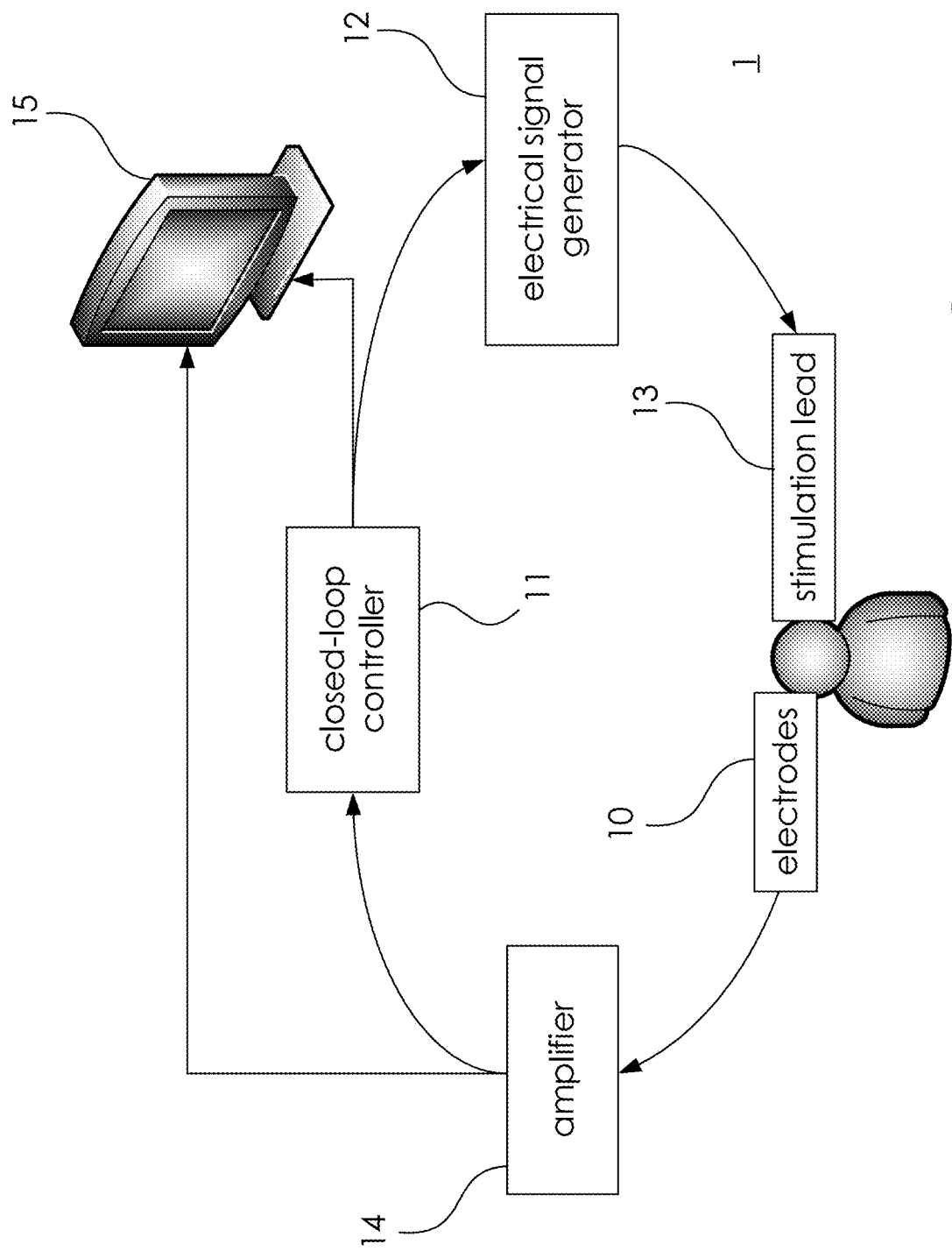
FIG. 7 illustrates the system for the closed-loop treatment, according to some embodiments of the present disclosure.

FIG. 7 shows a system for treating movement disorders. In some embodiments, the system 1 includes a plurality of electrodes 10, a closed-loop controller 11, an electrical signal generator 12 and a stimulation lead 13. The electrodes 10 are disposed on the brain, configured to probe a first region of a brain of a patient with movement disorders and collect a central nervous signal of the patient. The closed-loop controller 11 is coupled to the electrodes 10, configured to identify the oscillation episode in the range of from about 3 Hz to about 20 Hz in the central nervous signal. The electrical signal generator 12 is coupled to the closed-loop controller 11, configured to generate stimulations. In some embodiments, the stimulations are triggered by the closed-loop controller 11. The stimulation lead 13 is coupled to the electrical signal generator 12, configured to deliver the stimulation to a second region of the patient.

In some embodiments, the electrodes 10 are microelectrodes for recording LFP signals in the extracellular space in brain. In some embodiments, the electrodes 10 are macroelectrodes for recording EEG signals on the surface of the scalp. In some embodiments, a recording instrument such as register, memory or storage (not shown in the figure) may be integrated in the system for assisting the recording of the signals, for example, saving the collected central nervous signals temporarily. In some embodiments, the first region that the electrodes probed and the second region that the stimulation lead stimulated may or may not be the same region. In some embodiments, the non-invasive technology of Transcranial Magnetic stimulation, focused ultrasound stimulation, and Transcranial direct-current stimulation may be used for recording EEG signals.

In some embodiments, the closed-loop controller 11 is a microcomputer with a microprocessor for computing to perform the analysis work in step S2 of the present disclosure. In some embodiments, a trigger is generated from the closed-loop controller 11 to the electrical signal generator 12.

In some embodiments, an amplifier 14 is coupled to the electrodes 10 and the closed-loop controller 11, configured to amplify the central nervous signal collected by the electrodes 10.

In some embodiments, the stimulation lead 13 is implanted to the brain to deliver the stimulation outputted from the electrical signal generator 12. In some embodiments, the stimulation lead 13 delivers the first stimulation and the second stimulation to subthalamic nucleus, globus pallidus, motor cortex, or somatosensory cortex of the patient. In some embodiments, the stimulation lead 13 is not implanted to the brain and some non-invasive systems such as transcranial magnetic stimulation, transcranial direct-current stimulation, and focused ultrasound may be used.

In some embodiments, a monitor 15 is wire or wirelessly connected to the amplifier 14 and the closed-loop controller 11, configured to monitor the central nervous signal. In some embodiments, the monitor 15 may display the EEG, the LFP or spectrogram regarding the observed oscillation episode in real time.

In one exemplary aspect, a method for treating movement disorders is provided. The method includes the following operations. A central nervous signal of a patient with movement disorders is recorded. A first stimulation is delivered from a stimulator to the patient when an oscillation episode in a range of from about 3 Hz to about 20 Hz is observed in the central nervous signal. The first stimulation is adapted when a measurable feature of the oscillation episode is altered.

In another exemplary aspect, a method for treating movement disorders is provided. The method includes the following operations. A closed-loop treatment is implemented. The closed-loop treatment includes the following operations. An oscillation of an electroencephalography (EEG) of a patient in a range of from about 3 Hz to about 20 Hz is identified. A non-invasive stimulation is delivered to the patient subsequent to identifying the oscillation.

In yet another exemplary aspect, a system for treating movement disorders is provided. The system includes a plurality of electrodes, a closed-loop controller, an electrical signal generator, and a stimulation lead. The plurality of electrodes is configured to probe a first region of a brain of a patient with movement disorders and collect a central nervous signal of the patient. The closed-loop controller coupled to the electrodes is configured to identify an oscillation episode of the central nervous signal in the range of from about 3 Hz to about 20 Hz in the central nervous signal. The electrical signal generator is coupled to the closed-loop controller and is configured to generate a stimulation. The stimulation lead is coupled to the electrical signal generator, and is configured to deliver the stimulation to a second region of the brain of the patient.

The foregoing outlines structures of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for treating Parkinson's disease, comprising:
recording a central nervous signal of a patient with Parkinson's disease;
identifying an onset of an oscillation episode from the central nervous signal, wherein the oscillation episode is a High-Voltage Spindle (HVS) signal having an oscillation frequency in a range of from about 5 Hz to about 13 Hz;
delivering a first stimulation from a stimulator to the patient when the onset of the oscillation episode is identified from the central nervous signal, wherein the first stimulation is applied during a course of the oscillation episode, and the first stimulation is terminated when the HVS signal is decaying to a lower threshold, terminated, or after the HVS signal being terminated for 1.0 to 2.0 seconds; and
adapting the first stimulation according to a measurable feature of the oscillation episode.

2. The method of claim 1, wherein adapting the first stimulation comprises lowering an intensity of the first stimulation.

3. The method of claim 1, wherein adapting the first stimulation comprises changing an application form of the first stimulation.

4. The method of claim 1, wherein the measurable feature of the oscillation episode comprises an oscillation intensity, the oscillation frequency, an energy derived from the oscillation episode, an oscillation duration, a frequency of occurrence of the oscillation episode, or the combinations thereof.

5. The method of claim 1, wherein the central nervous signal of the patient is observed by monitoring local field potentials (LFP) or electroencephalography (EEG) recordings.

6. The method of claim 5, wherein the lower threshold and the termination of the HVS signal is determined by a time-frequency analysis or second-order statistic algorithm based on the LFP recordings.

7. The method of claim 6, wherein the time-frequency analysis or the second-order statistic algorithm further determine an oscillation duration of the oscillation episode to be in a range from 1 to 4 seconds.

8. The method of claim 1, wherein delivering the first stimulation comprises applying electrical stimulations with a frequency in the range of from about 100 Hz to about 180 Hz.

9. The method of claim 1, wherein delivering the first stimulation comprises applying electrical stimulations with a frequency in the range of about 10 Hz to about 10K Hz.

10. The method of claim 1, further comprising:
recording the measurable feature of the oscillation episode before or during delivering the first stimulation, the measurable feature comprises at least one of an oscillation intensity, the oscillation frequency, an oscillation duration of the oscillation episode, and a frequency of occurrence of the oscillation episode within a predetermined timeframe.

11. The method of claim 10, wherein adapting the first stimulation according to the measurable feature of the oscillation episode comprises concurrently adjusting the first stimulation when at least one of the oscillation intensity and the oscillation frequency changes.

12. The method of claim 10, further comprising determining a stimulation form according to the measurable feature, wherein the stimulation form comprises at least one of a stimulation frequency, a stimulation intensity, and a stimulation waveform.

13. The method of claim 12, further comprising delivering a second stimulation subsequent to terminating the first stimulation when another oscillation episode is observed in the central nervous signal, wherein the second stimulation is applied with the stimulation form determined by at least one of the oscillation duration of the oscillation episode and the frequency of occurrence of the oscillation episode within the predetermined timeframe.

14. The method of claim 13 wherein the second stimulation is applied during a course of the another oscillation episode.

15. The method of claim 14, wherein the second stimulation has a second stimulation duration, a duration of the second stimulation is adapted to be about 70% or about 80% shorter than a duration of the first stimulation.

16. The method of claim 1, wherein the stimulator is an implanted electrical signal generator or a non-invasive system of transcranial magnetic stimulation, current stimulation, or focused ultrasound.

17. The method of claim 1, further comprising implanting a stimulation lead coupling to the electrical signal generator to a second region of a brain of the patient prior to recording the central nervous signal of the patient from a first region of the brain, wherein the first region is different from the second region.

18. The method of claim 1, wherein the stimulation duration of the first stimulation is shorter than the oscillation duration of the oscillation episode.

19. The method of claim 1, wherein the onset of the oscillation episode is identified within 0.3 second by applying a continuous wavelet transform (CWT), and the first stimulation is delivered immediately thereafter.

20. The method of claim 1, further comprising:
pausing the first stimulation during the course of the oscillation episode before the first stimulation is terminated.

* * * * *